United States Patent [19]

Naylor

[11] Patent Number: 4,865,546
[45] Date of Patent: Sep. 12, 1989

[54] METHODS FOR MANUFACTURE, REPAIR AND MODIFICATION OF DENTURES

[76] Inventor: Merlin E. Naylor, 131 Chesterfield Dr., Bogart, Ga. 30622

[21] Appl. No.: 93,299

[22] Filed: Sep. 4, 1987

Related U.S. Application Data

[63] Continuation-in-part of Ser. No. 838,172, Mar. 10, 1986, abandoned.

[51] Int. Cl.$^4$ ............................................. A61C 11/00
[52] U.S. Cl. ..................................... 433/213; 433/60; 433/214; 264/17
[58] Field of Search .................. 433/213, 214, 49, 57, 433/60; 264/16, 17

[56] References Cited

U.S. PATENT DOCUMENTS

| | | | |
|---|---|---|---|
| 1,517,922 | 12/1924 | Stanley | 433/57 |
| 2,616,175 | 11/1952 | Buhler | 433/213 |
| 4,195,047 | 3/1980 | Drennan et al. | 264/17 |
| 4,300,883 | 11/1981 | Mier | 433/49 |
| 4,381,947 | 5/1983 | Pellico | 433/213 |
| 4,436,511 | 3/1984 | Mitchell | 433/49 |
| 4,439,151 | 3/1984 | Whelan | 433/60 |

*Primary Examiner*—John J. Wilson
*Attorney, Agent, or Firm*—Hubbard, Thurman, Turner & Tucker

[57] ABSTRACT

A method is disclosed for making a resilient cast by using impression material to fill any mold, such as an impression of an enucleated eye socket, an impression of the oral cavity, an impression of the tissue bearing surface of a denture, or any other mold in which it would be advantageous to have a resilient model on which to acomplish work. More specifically, a unique method and apparatus for performing a wide variety of procedures relating to the fabrication, repair and equilibration of dentures is provided. A non-reversible hydrocolloid impression compound, such as alginate, is used to form resilient denture casts supported on a support platform to provide a stable work surface. A similar support platform is incorporated in the base of an articulator, used for the mounting dentures in centric relationship directly from the patient's mouth in a method for correcting of occlusal discrepancies. An improved method for the repair of a cracked or broken denture is provided, wherein a resilient cast is formed of the denture by pouring up impression material into the tissue bearing surface thereof. Also, a novel method for the construction of a provisional denture is disclosed. The impression material is used to form a resilient positive cast of the patient's mouth and teeth.

24 Claims, 5 Drawing Sheets

METHODS FOR MANUFACTURE, REPAIR AND MODIFICATION OF DENTURES

CROSS REFERENCE TO RELATED APPLICATION

This application is a continuation-in-part of U.S. patent application Ser. No. 838,172, filed Mar. 10, 1986, entitled "A Process for Repairing and Modifying Dentures", now abandoned.

BACKGROUND OF THE INVENTION

The present invention relates generally to a method of making a resilient cast by using impression material to fill any mold, such as an impression of an enucleated eye socket, an impression of the oral cavity, an impression of the tissue bearing surface of a denture, or any other mold in which it would be advantageous to have a resilient model on which to accomplish work. More specifically, the invention relates to the repair, fabrication and correction of occlusal discrepancies in dentures using an impression material to make a resilient cast.

The inconvenience and discomfort associated with dentures has to a large degree been minimized with the advancement of modern dentistry. However, most procedures relating to the repair of dentures are costly, time consuming and have not kept pace with the advancements in dentistry.

The traditional process of repairing a broken denture dates from the conception of using acrylic resin for denture construction. This repair process consists of temporarily luting the broken pieces into apposition prior to making a plaster cast to index the broken pieces. The broken edges are then ground to receive quick setting repair acrylic. The broken pieces may be removed and replaced on the cast after the broken edges have been prepared to receive repair acrylic. This procedure is complicated and rendered ineffective if the denture has undercuts whereby the denture is locked to the unyielding cast and cannot be removed. This problem can be partially overcome by blocking out the large undercuts in the denture with wet tissue paper before pouring the plaster. If the denture cannot be removed from the cast, it must be prepared on the cast by grinding along the broken edges. An inadequate preparation usually results in the preparation of a ditch to receive the repair acrylic. In addition to a less than ideal preparation, there is a danger of plaster contaminating the repair acrylic. Further, another problem associated with traditional methods is the danger of mutilating the cast if the denture is ground on the cast, resulting in defects on the tissue surface of the denture.

With regard to the fabrication of dentures, dentures that are inserted immediately following extraction of teeth are traditionally fabricated without regard to the shape or position of the teeth that are being replaced. In other words, the immediate denture is constructed by cutting off the plaster or artificial stone teeth from their cast and proceeding to fabricate a denture as if it were a normal edentulus case. There are several disadvantages to this procedure. For example, the occlusion is never exactly correct which causes non-stable dentures that produce sore spots and entail much time spent on equilibrating the denture. Tissue recovery material is normally used as the healing process changes the topography of the mouth. After complete healing, the intermediate denture must be relined or a complete new denture must be made to satisfy the criteria of an acceptable denture. In spite of the shortcomings of intermediate dentures, there are occasions when it is necessary or desirable not to use a laboratory "permanent" denture. The temporary denture is made quickly in the office and can be a valuable transitional denture during the healing period following surgery. If the denture duplicates the same occulision, the same vertical dimension and feels the same as the natural teeth, the patient will become conditioned to wearing a denture very quickly. After healing takes places, a "permanent denture" can be made that does not have to be relined so soon. A temporary intermediate denture possessing these qualities has heretofore been unavailable prior to applicant's invention.

Another problem experienced by denture wearers are sore spots caused by occlusal discrepancies in the patient's bite, in which premature cuspal contact causes shifting of the dentures, applying localized pressure to the oral tissue. Procedures are often performed by the dentist in an effort to quickly and immediately address the patient's discomfort. Correcting the occlusion is usually done by equilibration of the prematurities in the mouth. This method possesses many shortcomings, since the mouth is dark and wet and the procedure is time consuming causing the patient to become tired, resulting in a false bite. The dentures have a tendency to move, also giving false markings. The equilibration would be better achieved by transferring the dentures from the patient's mouth to an articulator, however there are currently several problems involved with this procedure. For example, original casts used for processing the dentures usually have been destroyed, and if present the dentures could not be made to fit them accurately. Plaster of paris cannot be used to mount the dentures to the articulator because most articulators require a thick base on the cast of the dentures which must be attached to the articulator. If it were possible to use plaster directly to form a cast in the denture the same problems would exist at removing and replacing the denture as previously described.

It is therefore an object of the present invention to provide for accurate and fast methods of denture fabrication, repair and equilibration procedures to eliminate or substantially minimize the above mentioned and other problems and limitations typically associated with current denture technology.

SUMMARY OF THE INVENTION

The present invention discloses a method of making a resilient cast by using impression material to fill any mold in which it would be advantageous to have a resilient model on which to accomplish work. The invention specifically provides a uniquely efficient method for the manufacture and repair of dentures using a resilient impression material as a casting material. A non-reversible hydrocolloid such as alginate is used to prepare resilient denture casts for accurately replicating the mouth tissue or denture during the various procedures described. A support platform for retaining a denture cast in a secure position is also provided in which the cast is secured to a cover on the platform by a portion of resilient impression material extruded through openings in the cover member thereof and becomes the base of the cast. Resilient denture casts may also be secured to an articulator for mounting dentures directly from the mouth thereto in centric relationship. The use of resilient impression material as denture casts to secure the dentures to the articulator provides a unique and accurate method for correction of occlusal discrepancies in dentures.

The steps utilized in a preferred method of repairing broken dentures as contemplated by the present invention may be performed quickly during a single office visit. The cracks or breaks in the denture are first temporarily fixed by intersecuring the pieces using a suitable bonding material. A resilient cast of the tissue bearing surface of the denture is then made by placing or pouring resilient casting material over the tissue bearing surface of the denture, and concurrently attaching it to a pre-formed solid base. The denture itself is then removed from the resilient cast and the pieces of denture are separated for preparation prior to final bonding. Typically, the adjacent surfaces of the denture must be filed or ground to a beveled edge to create an adequate surface area for this bonding step. In conventional denture repair methods, the result of this preparation of the denture is an unintentional alteration in the contours and alignment of the tissue bearing portion of the denture. In the present invention, however, this problem is solved by placing the respective pieces of the denture onto the resilient denture cast to achieve proper alignment before final bonding is performed. Suitable quick setting acrylic material is then deposited into the prepared area between the denture pieces. Once the acrylic has hardened, the denture may be removed and placed again into the patient's mouth. The accuracy achieved by this novel form of repair eliminates considerable discomfort in the fit of the denture for the patient and may be performed quickly.

The present invention also provides a novel method for fabrication of provisional or intermediate dentures which can be inserted intermediately after surgery supplying the same occlusion, the same appearance, and the same feel as the natural dentition, to be worn until healing takes place after surgery. In such methods, resilient impression is first used to create an impression of the patient's mouth tissue and teeth. Tooth shade acrylic material is then placed within selected ones of the tooth depressions in the impression to form acrylic teeth which correspond to the teeth to be replaced. Resilient impression material is then poured into the impression covering the acrylic teeth and placed on an alginate retaining device which forms the base of the resilient cast. This positive cast is then removed and the acrylic artificial teeth previously formed in the impression are aligned in proper position on the resilient cast. Next, acrylic material is sprinkled or placed into the cast to form the denture base and join the previously made acrylic teeth thereto. The denture may then be removed from the resilient cast and prepared for delivery. The use of the resilient casting material for this purpose uniquely provides the dentist with the ability to quickly form a temporary denture without delay, that will serve the purpose of enabling the patient to become accustomed to wearing a denture during the healing process awaiting a permanent denture.

The present invention also provides a unique method for correcting occlusal discrepancies in dentures. In connection therewith, there is provided an articulator for mounting dentures thereto directly from the mouth. A resilient impression material is placed on the support platform of the articulator and extruded through openings in a cover member to provide a base for the lower mandibular denture cast. The upper arm element of the articulator includes an upper platform having an opening for receiving resilient impression material. The resilient impression material retained therein holds the upper resilient denture cast and denture.

The present invention's placement of the dentures on resilient casts enables the dentist to mount the dentures directly from the mouth onto the articulator. First, a bite registration material is placed in the patient's mouth to obtain a registration of the teeth in their proper centric relationship. A mandibular resilient cast is formed directly on the articulator or base of the cast being the articulator itself. The bite registration material is then placed over the lower denture in proper alignment, corresponding to the impression previously obtained in the mouth. Next, the upper denture is placed on the bite registration material on the lower denture to align the upper denture in proper centric relation thereto. The upper arm of the articulator is lowered so that the fluent casting material can flow through the upper platform hole to the upper denture. The bite registration material is removed, and the dentures are free to move relative to one another in proper centric relationship. Carbon paper or other marking material may then be placed between the dentures to mark the prematurities, which may then be removed very accurately to thereby properly align the upper and lower dentures.

DETAILED DESCRIPTION

Figure 1:
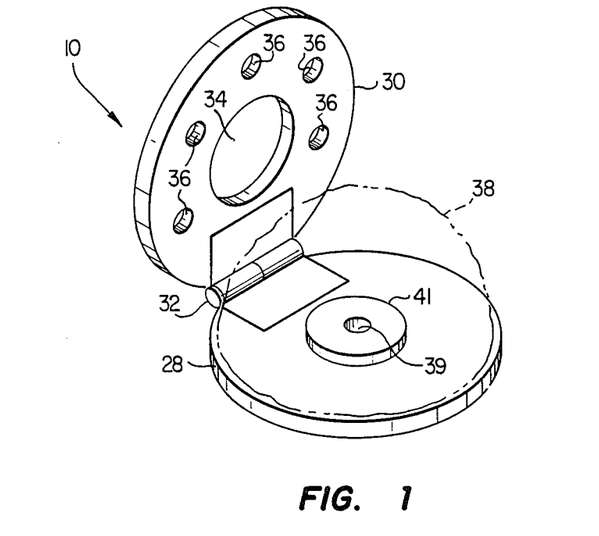
FIG. 1 is a perspective view of a support platform of the present invention which supports a resilient denture cast used in a denture repair method of the present invention, showing the cover in an open position and a portion of resilient impression material (in phantom) placed over its base.
Figure 2:
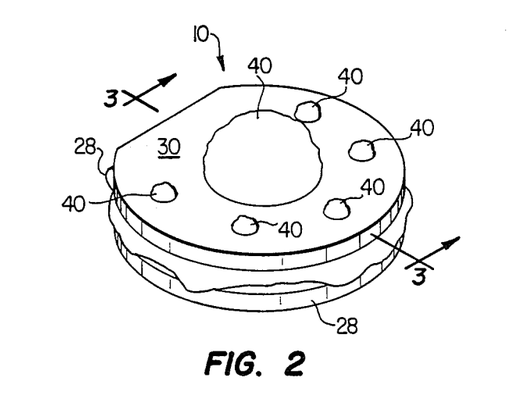
FIG. 2 is a perspective view of the support platform, showing the cover in the closed position such that the resilient impression material is partially extruded through openings in the cover.
Figure 3:
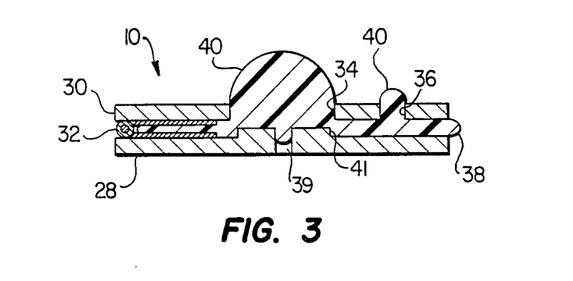
FIG. 3 is a cross-sectional view through the support platform 10, taken along line 3—3 of FIG. 2, and illustrates the relative positioning of the base, cover and resilient impression material when the cover is in the closed position.

The present invention provides unique methods of performing a wide variety of procedures relating to making a resilient cast using impression material to fill any mold in which it would be advantageous to have a resilient model on which to accomplish work. Specifically, the invention herein sets forth related procedures for the fabrication and repair of dentures. A non-reversible hydrocolloid alginate is utilized to form resilient denture casts as herein described. The alginate (or resilient "impression material") is also utilized in conjunction with a support platform 10 as shown in FIGS. 1-3, to form the base of a resilient cast to stabilize the stable work surface during repair or fabrication procedures. A similar support platform 12 is incorporated in the base of articulator 14 (FIG. 15), used for the mounting of resilient denture casts and dentures in centric relationship directly from the patient's mouth in the correction of occlusal discrepancies.

Figure 4:
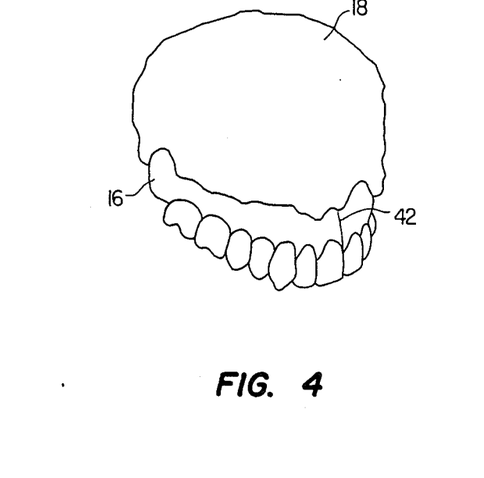
FIG. 4 is a perspective view of a cracked, temporarily intersecured upper denture having a portion of resilient casting material poured into the upper tissue bearing surface of a denture thereof to form a resilient denture cast.
Figure 5:
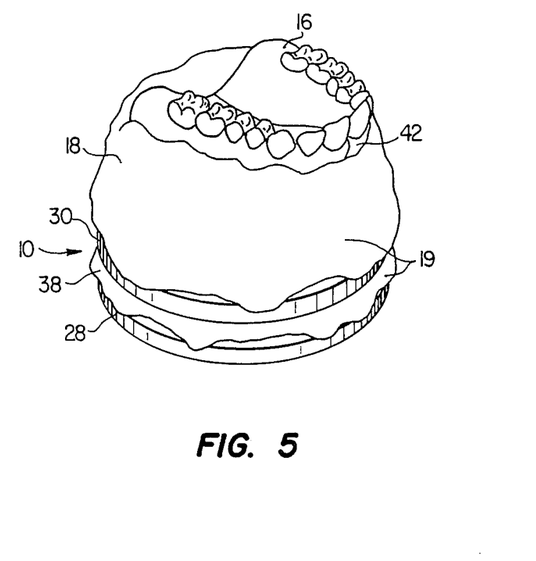
FIG. 5 is a perspective view showing the denture of FIG. 4 and the resilient cast attached thereto in an inverted position and joined to the extruded portion of resilient casting material and cover of the support platform to form a resilient cast.
Figure 6:
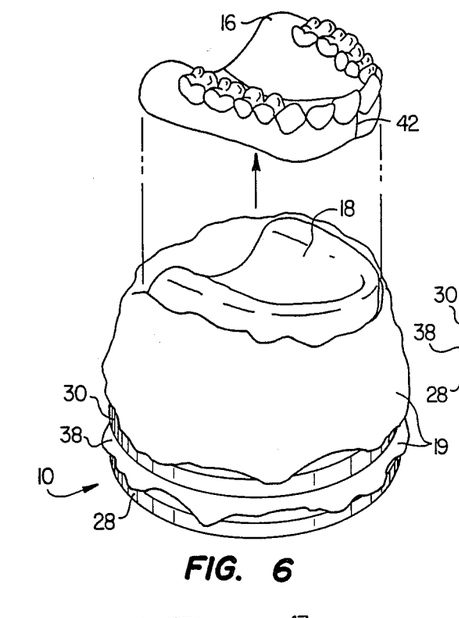
FIG. 6 is a partially exploded perspective view of the denture and resilient cast as joined to the support platform, showing the resilient cast conforming to the contours of the upper tissue bearing surface of the denture as the denture is removed therefrom.

Referring briefly to FIGS. 1-7, there is shown an improved method for the repair of a cracked or broken denture 16. A resilient impression 18 is formed by flowing a portion an alginate mix (impression material) into the denture 16 (FIG. 4) and the remainder of the mix onto support platform 10, and joining the impression 18 onto platform 10 to form denture cast 19 (FIG. 5).

Figure 7:
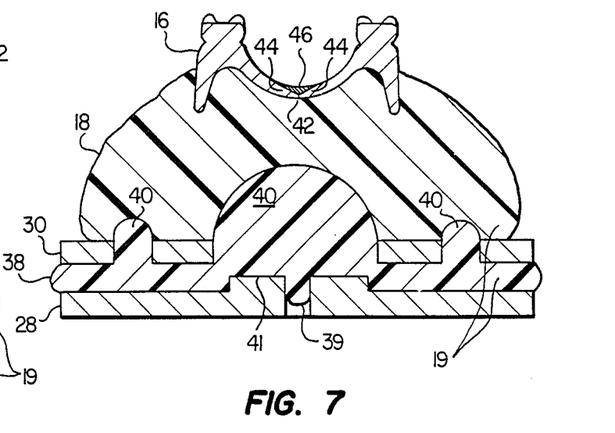
FIG. 7 is an enlarged, side elevational view of the denture, resilient cast and support platform showing the denture placed in alignment over the resilient cast after repair preparation procedures have been performed and acrylic bonding material applied to the fracture of the denture.
Figure 8:
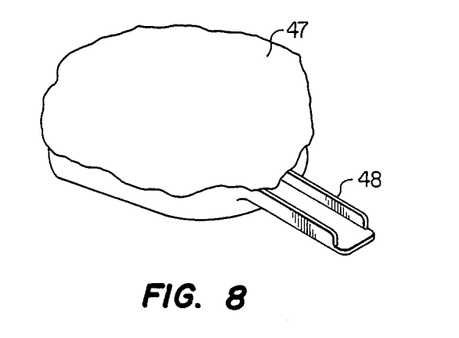
FIG. 8 is a perspective view of an oral impression tray having deposited therein a portion of resilient casting material used in a denture fabrication method of the present invention.
Figure 9:
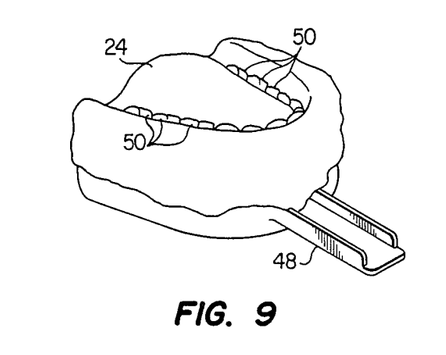
FIG. 9 is a perspective view of the oral impression tray containing an impression of the oral cavity and illustrates an impression of the oral tissue and teeth.

FIGS. 6-14 depict a novel method for the construction of a provisional denture 20. The alginate or resilient impression material is used to form a resilient positive cast 22 of the patient's mouth poured from impression 48 (FIG. 9). Artificial teeth 26 are constructed by deposition of tooth shape acrylic into impression 48. The artificial teeth 26 are subsequently positioned on positive cast 22 for incorporation into denture 20.

Finally, FIGS. 15-21 depict a novel method for the correction of occlusal discrepancies of dentures. The dentures are mounted to articulator 14 in a manner which will be subsequently described. The prematurities of the teeth are thereby accurately detected with the dentures mounted in centric relationship on the articulator.

The resilient casting material utilized in the present invention is preferably a non-reversible hydrocolloid compound such as alginate. Alginate is well suited for the purposes herein for the reason that it sets quickly and is generally commercially available, and found in most dentist's offices. A resilient cast can be formed by pouring up an impression of the mouth on the tissue bearing surface of the denture, and then adhering to a retention base. Various forms of hardware such as support platforms 10 and 12 are therefore reuseable since the casting material may be easily removed therefrom for repetitive use.

Referring initially to FIGS. 1-3, there is shown a preferred method for utilizing resilient casting material in conjunction with support platform 10 to provide a stable cast work surface. The support platform 10 as herein described may, of course, be replaced with an alternately configured platform, the function of which is to merely adequately retain the resilient casting material thereon. A support platform is desired for use in and facilitates performance of delicate work on the dentures. The adhesion of casts to the platform is accomplished by the use of a portion of resilient casting material attached to the platform which also joins to the cast.

In a preferred embodiment thereof, support platform 10 includes a base portion 28 and has a cover member 30 pivotally secured thereto by suitable hinge means 32. Cover 30 also has formed therethrough a central aperture 34 and a circumferentially spaced series of apertures 36 spaced radially outwardly therefrom also on cover 30. A portion of resilient impression material, generally designated by the numeral 38, is placed over base portion 28 in a manner sufficient to generally cover the surface thereof. As cover 30 is closed, portions 40 of impression material 38 are extruded through apertures 34 and 36 and extend generally upwardly as shown in FIG. 3. An elevated platform 41 is situated on base 28 to facilitate the extrusion of the impression material upwardly through aperture 34. A small hole 39 in platform 41 also receives a portion of impression material 38 to improve the anchoring characteristics of material 38 to platform 10. Portions 40 may thereby be joined to denture impression 18 which is inverted and placed over cover member 30. Impression 18 bonds to cover 30 and portions 40 to provide a cast 19 creating a steady work base which does not shift during the various procedures performed in conjunction with the dentures 16. Platform 10 is designed to be reusable. Upon completion of the particular task, the cast may be separated from platform 10, cover 30 may be pivoted to an open position, and the impression material 38 evacuated.

The method for repair of dentures as contemplated by the present invention specifically referred to in FIGS. 1-7 utilizes resilient impression material to quickly and accurately perform a denture repair. The formation of denture cast 19 enables the dentist to maintain an adequate record of the denture to effect an accurate repair. Denture 16 has, for example, break 42 which is temporarily held in place by bonding material. Resilient casting material may then be poured or placed into the tissue bearing surface of denture 16 as shown in FIG. 4 to create an accurate denture cast. Alginate-impression material filled denture therein is inverted and joined to support platform 10 as shown in FIG. 5. Impression 18 is adequately secured thereto by portions 40 extending upwardly through cover 30, as previously described. Denture 16 may then be removed from cast 18 so that it can be prepared and returned to the flexible cast for repair. Because of the resilient nature of the casting material forming denture cast 19, denture 16 does not become locked to the cast by the undercuts therein. Likewise, the cast retains its record of the denture topography due to its resilient qualities. Next, the denture pieces are separated so that the adjacent surfaces of break 42 may be prepared to receive repair acrylic. The normal procedure is to bevel the adjacent surfaces such that an adequate surface area 44 is present to receive the repair acrylic 46. The denture 16, is replaced over the cast 19 to properly align and position each piece thereof as shown in FIG. 7. A quick setting repair acrylic 46 is then placed along break 42 and permitted to harden. Denture 16 is now accurately repaired, and may be removed for delivery. The method as described herein permits the repair to be accomplished in the dentist's office in a short time span without compromise of accuracy.

Figure 10:
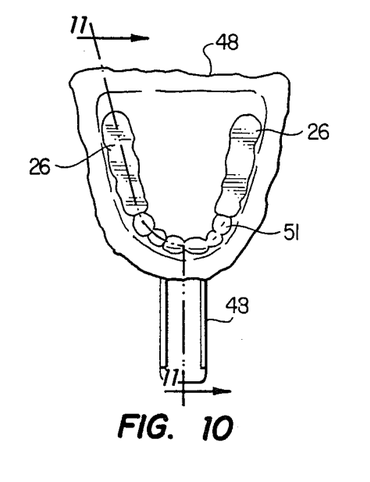
FIG. 10 is a top plan view of the impression of FIG. 9 showing tooth-shade acrylic deposited in selected tooth depressions formed in the impression.
Figure 11:
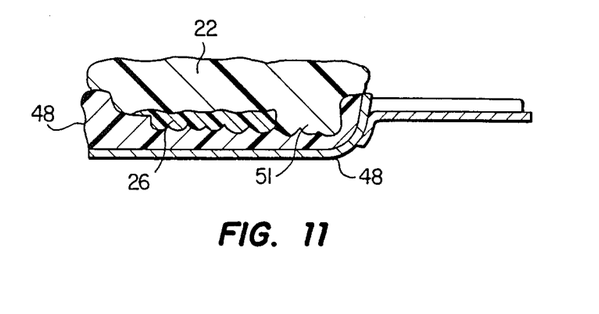
FIG. 11 is a cross-sectional view, taken along line 11—11 of FIG. 10, showing a portion of impression material or alginate poured into the impression and over the acrylic teeth to create a resilient positive cast of the remaining tooth depressions and mouth tissue.
Figure 12:
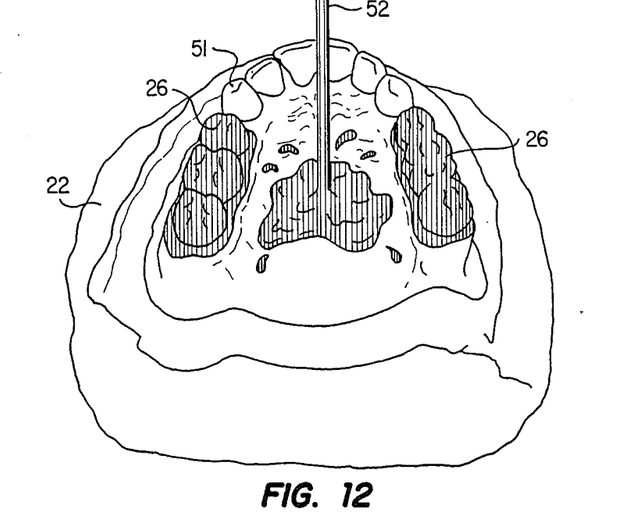
FIG. 12 is an enlarged scale perspective view of the resilient cast of FIG. 11, removed from the impression tray, and inverted, showing the acrylic teeth properly positioned on the resilient cast and also showing placement of acrylic material onto the cast.

Referring now to FIGS. 8-14, there is depicted the novel method of fabricating a provisional denture utilizing resilient impression material or alginate to construct a cast upon which an acceptable denture may be fabricated within a short period of time. An impression is taken of the mouth prior to extracting teeth (FIG. 9). The voids of the teeth to be extracted are filled with a tooth shade quick setting acrylic up to the gingival border (FIG. 10). The impression is then poured with alginate, covering the acrylic teeth (FIGS. 11 and 12). The alginate filled tray is then inverted over the supporting device. The ungelled alginate in the tray and supporting structure upon gelling to a semi-solid will become the resilient cast upon which the temporary denture will be fabricated. Examining this process in greater detail, and as seen in FIGS. 8 and 9, a portion of resilient impression material 47 is placed into a conventional impression tray 48. After placement in the patient's mouth, the impression 24 is formed in the impression material 47 and corresponds to the patient's mouth tissue and teeth. The tooth depressions 50 represent the shape of the patient's actual teeth, and these voids are used to construct the artificial teeth 26 and positive cast 22. Once impression 24 has been formed, artificial tooth forming material is placed into selected ones of tooth depressions 50 up to the gingival border as shown in FIG. 10, to form artificial teeth 26. After the acrylic tooth material is deposited within the selected depressions 50, casting material may be pressed into impression 24 to create a resilient positive cast 22 (FIG. 11). Cast 22 corresponds to the patient's mouth tissue (as seen clearly in FIG. 12) and also replicates the patient's original teeth 51. The cast 22 covers the previously formed artificial teeth 26 which are later formed into the final denture 20.

Figure 13:
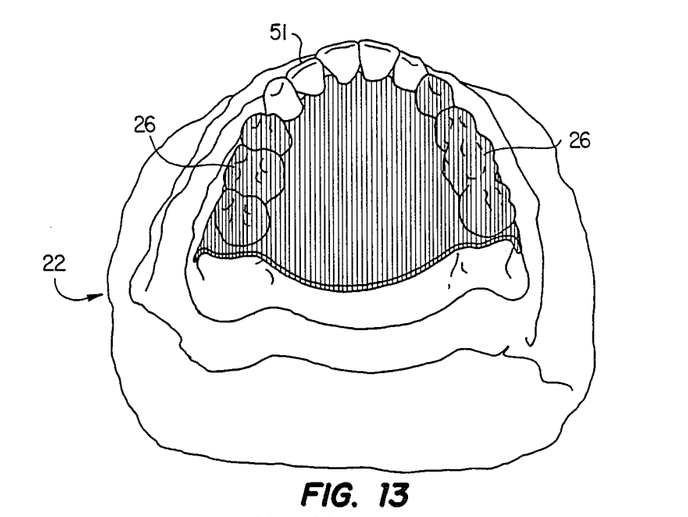
FIG. 13 is an enlarged scale perspective view of the resilient cast showing acrylic material as placed over the tissue bearing portion of the cast connecting the acrylic teeth to form a denture.
Figure 14:
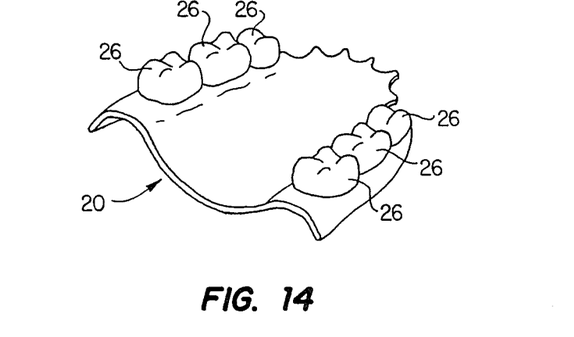
FIG. 14 is an enlarged, side perspective view of the denture removed from the resilient cast and ready for placement in the mouth.

Once positive cast 22 has set in the impression tray it is removed as shown in FIGS. 12 and 13. The artificial teeth 26 are placed in their respective positions over cast 22. As further shown in FIG. 12, acrylic resin 52 used to form the denture base is then spread over the surface of the cast. Acrylic 52 bonds to artificial teeth 26 and conforms generally to the area defined by the cast. The teeth 51 on cast 22 define the contours of the acrylic 52 to provide a proper denture fit, as seen in FIG. 13. Provisional denture 20 is thereby formed and may be removed from cast 22 as shown in FIG. 14. Dentures 26 may then be polished or otherwise finished for placement in the mouth.

The construction of a provisional denture in this manner results in a greatly improved denture fit through the use of the resilient cast and at the same time permits dentures to be fitted immediately after tooth extraction while the patient is in the office. The patient may, therefore, become used to wearing dentures that are a replica of his natural dentition and the transition to "permanent" dentures after healing has taken place will be easier.

Figure 15:
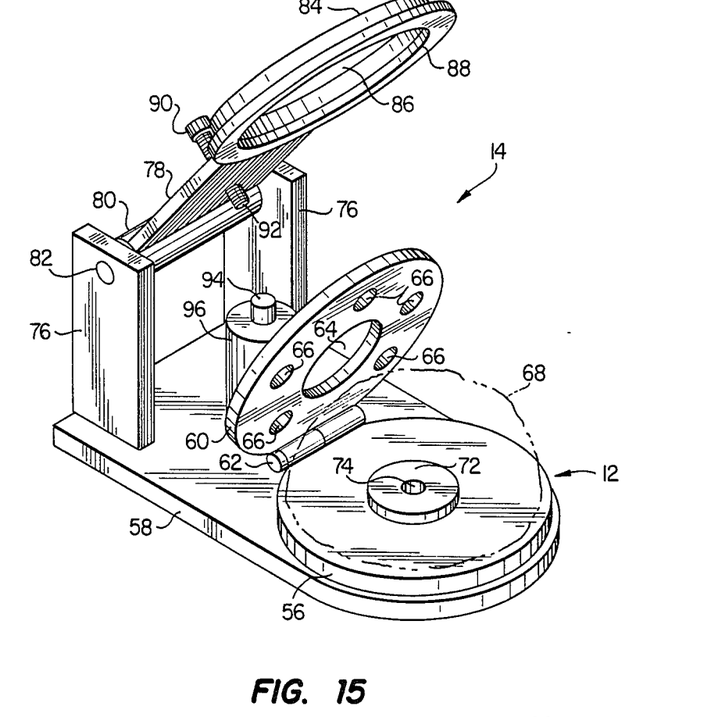
FIG. 15 is a perspective view of an articulator of the present invention showing in phantom a portion of resilient impression material placed on the base of the support platform.
Figure 16:
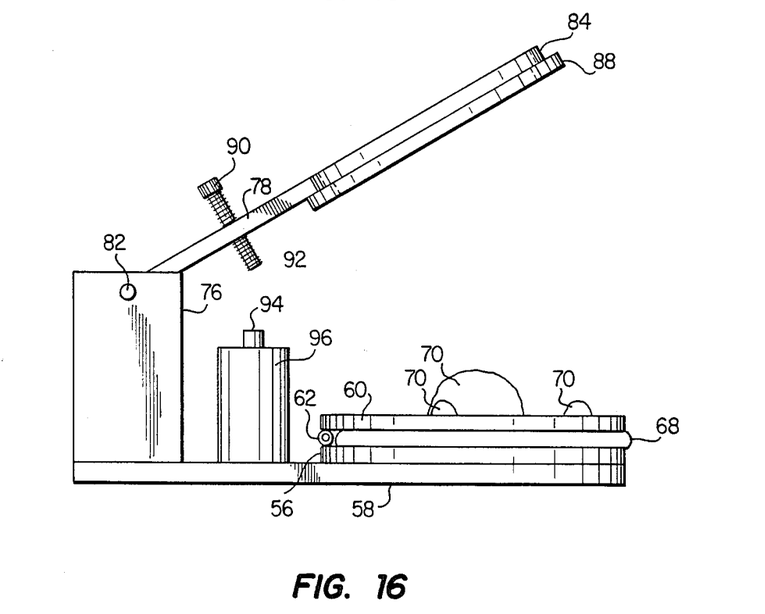
FIG. 16 is a side elevational view of the articulator showing the cover of the support platform in a closed position and having a portion of resilient impression material partially extruded therethrough.

The unique method of correction of occlusal discrepancies contemplated by the present invention is shown in FIGS. 15-21. Articulator 14, as shown in FIGS. 15 and 16, is used to mount a patient's dentures thereon in centric relation for the proper detection and marking of denture prematurities. The dentures may be quickly and easily placed on the articulator and also removed therefrom during the occlusal equilibration process, due to the use of the resilient alginate casts and impression material as described herein to attach the dentures to articulator 14. The support platform 12 of articulator 14 is essentially the same as the support platform 10 subsequently described with reference to FIGS. 1-3. As with support platform 10, it is contemplated that various alternative support platforms may be used which also adequately retain dentures in a steady position. In the preferred embodiment, support platform 12 is adhered at its base 56 to support skid 58. Cover 60 is pivotally secured to platform 12 by hinge means 62. Cover 60 also has formed therethrough a central aperture 64 and a circumferentially spaced series of apertures 66 spaced radially outwardly therefrom. A portion of resilient impression material 68 shown in phantom in FIG. 15 is placed over base 56, and is used as described herein for mounting a cast, similar to the method previously described. As cover 60 is closed, portions 70 of impression material 68 are extruded through apertures 64 and 66. Elevated pad 72 is oriented on base 56 beneath central aperture 64 and serves to facilitate extrusion of casting material therethrough. A small opening 74 centrally located on pad 72 serves to anchor casting material 68 securely to support platform 12. The support platform 12 in this manner serves to receive and secure a lower denture cast. Elevated pillars 76 located on support skid 58 have joined thereto upper arm 78, for retaining the upper denture cast. A suitable pin member 80 secures the upper arm 78 to support pillars 76 through hinge sockets 82. Upper arm 78 is therefore pivotable relative to support skid 5 and includes at the distal end thereof an upper platform 84. Upper platform 84 may be oriented directly above support platform 12, and the opening 86 in upper platform 84 serves to receive and retain a portion of resilient impression material 87. Resilient impression material 87 is retained therein in part due to annular rim 88 circumscribing the diameter of opening 86. An adjustment screw 90 is threadingly disposed through upper arm 78 to adjust the elevation thereof. The point 92 of screw 90 bears on pad 94 of pillar 96.

The correction of occlusal discrepancies utilizing articulator 14 of the present invention is performed by the steps generally outlined in FIGS. 16–21. Resilient impression material is pressed into the upper denture 98 and lower denture 100 to form upper denture cast 102 and lower denture cast 104 in a manner similar to that described with reference to FIGS. 4–6. The resilient casting material will retain the dentures therein yet permit removal thereof without disturbing the recorded denture topography. The impression material now retained by articulator 14 will be used as shown to retain upper denture cast 102 and lower denture cast 104 securely on articulator 14 in centric relationship.

Figure 18:
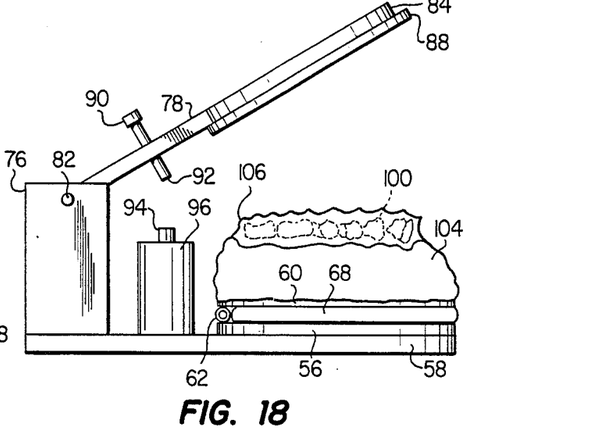
FIG. 18 is a reduced scale side elevational view of the articulator showing an occlusal registration material placed on the lower denture.

In order to adequately correct occlusal discrepancies, the patient's bite must be in proper centric relation, or the denture prematurities cannot accurately be marked. A common problem with "spot grinding" dentures directly in the patient's mouth is that the patient's jaw tends to shift as the jaws open and close. The prematurities in the teeth cannot thereby precisely be determined. In order to establish the proper centric relationship of the dentures one to another, a bite registration 106, as shown in FIG. 18 over the lower denture 100, is taken while the dentures are in the patient's mouth. Typically, bite registration material is a deformable, somewhat resilient material placed in the patient's mouth over the lower dentures. As the patient closes his bite in proper centric relation, an occlusal record is established on bite registration 106 providing depressions on either side thereof corresponding to the lower teeth and upper teeth. The bite registration 106, once taken from the patient's mouth, is then set aside for use as will be subsequently described.

Figure 17:
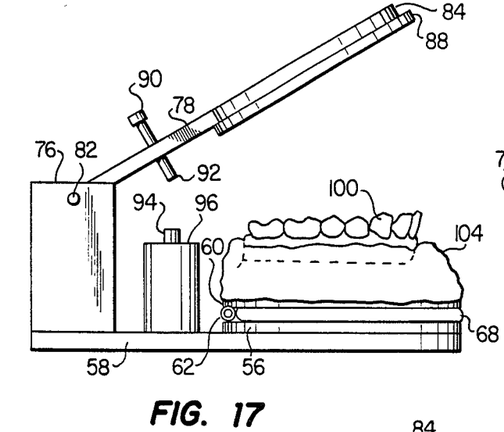
FIG. 17 is a reduced scale side elevational view of the articulator having a resilient cast and denture joined to the lower member of the articulator.
Figure 19:
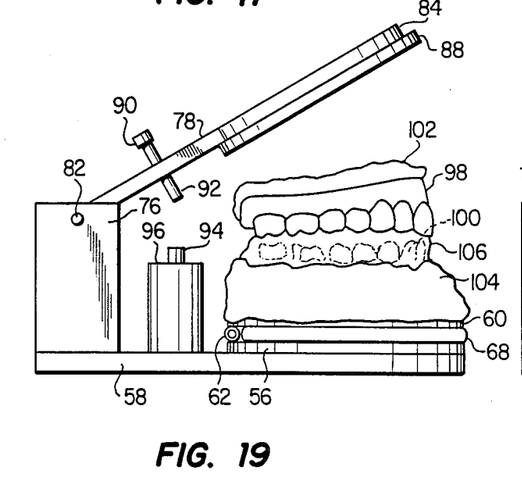
FIG. 19 is a reduced scale side elevational view of the articulator showing a maxillary denture placed over the occlusal registration material corresponding to the index therein to place the upper and lower dentures in centric relationship.
Figure 20:
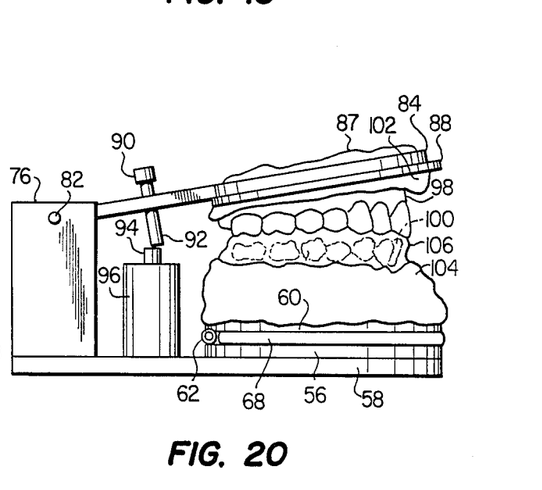
FIG. 20 is a reduced scale side elevational view of the articulator showing the dentures mounted on the upper arm of the articulator.
Figure 21:
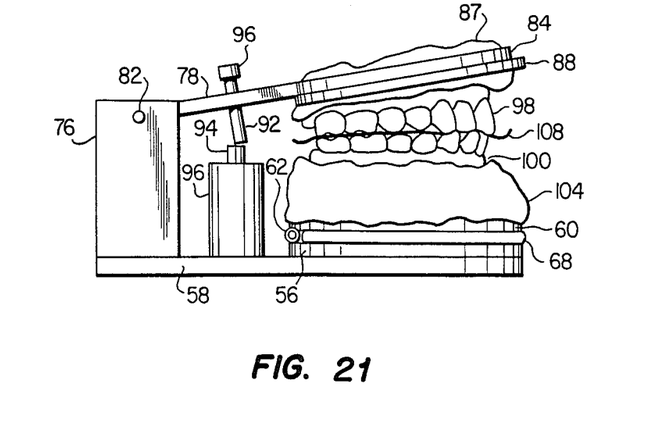
FIG. 21 is a reduced scale side elevational view of the articulator showing the registration material removed from between the upper and lower dentures, and a portion of carbon paper placed therebetween for marking of prematurities of the dentures in centric relation.

The manibular denture 100 and its corresponding lower denture cast 104 are mounted to support platform 12 (FIG. 17). Bite registration 106, previously taken while the dentures were in the mouth, is then placed on lower denture 100 in proper alignment to correspond to the impressions thereon previously taken while the teeth were closed together in centric (FIG. 18). Maxillary denture 98 is then lowered onto bite registraton 106 in alignment with the depressions previously obtained from the mouth (FIG. 19). In this manner, the upper denture 98 and lower denture 100 are now in proper centric relationship. Next, as shown in FIG. 20, the upper arm 78 is lowered such that the impression material may be placed within opening 86 joining the upper denture cast 102 and becoming fixed thereto. As shown with reference to FIG. 21, bite registration 106 is removed and upper arm 78 may be pivoted to raise and lower the dentures in centric relation. A carbon or other marking material 108 may be placed between the dentures such that when they meet, the prematurities or high spots on the dentures are marked. The dentures may then be equilibrated by accurately removing the prematurities. Once the prematurities are removed, the dentures 98 and 100 may be easily detached from casts 102 and 104 and placed in the patient's mouth to check results. If necessary, the process may be repeated.

It can be seen from the foregoing that the present invention provides a method for the fabrication, repair and equilibration of dentures which is relatively simple, fast and precise, and is readily adaptable to a wide variety of applications. Due to the unique use of impression material to form resilient denture casts, dentures may be fabricated or repaired directly from the mouth in a short period of time, the dentures being easily removed from the cast without the common problems associated with plaster of paris such as locking beneath undercuts. Additionally, the unique support platform used for retaining the resilient casts provides a serviceable unit for maintaining the work piece in the steady position. The articulator used for the correction of occlusal discrepancies as set forth herein is uniquely adaptable to receive impression material and thus retain then denture casts thereon in centric relation taken directly from the patient's mouth.

The foregoing detailed description is to be clearly understood as being given by way of illustration and example only, the spirit and scope of the present invention being limited solely by the appended claims.

What I claim is:

1. A method of forming a resilient cast or model by pouring a suitable settable fluent material into a mold, said method comprising the steps of:
   using alginate impression material as the settable fluent material;
   pouring said alginate into a suitable mold;
   placing alginate onto a solid supporting base for the ingress of said alginate under retentive undercuts;
   inverting said mold onto said base thus unitizing the alginate of said mold with the alginate of said base;
   removing said mold after said alginate has set;
   revealing a resilient cast.

2. The method according to claim 1 wherein:
   said mold may be the tissue bearing surface of a broken denture into which alginate is poured to produce a resilient cast to be used for the repair of said denture.

3. The method according to claim 1 where:
   said mold may be an impression of the oral cavity into which alginate is poured to produce a resilient cast of the mouth to facilitate construction of a denture.

4. The method according to claim 1 wherein:
   said mold may be an impression of the socket of an enucleated eye into which alginate is poured to create a resilient cast to facilitate producing a prosthesis by a process well known to those familiar with the art.

5. The method according to claim 1 wherein:
   the settable fluent material is a non-reversible hydrocolloid.

6. A method of rapidly and accurately correcting occlusal discrepancies of dentures by transferring said dentures from the mouth to an articulator, said method comprising the steps of:
   using a bite registration material to record the occlusal relationship of the dentures while the patient's jaws are in centric relationship;
   removing the dentures and bite registration from the mouth;
   placing alginate into the mandibular denture and onto the lower member of the articulator;

unitizing alginate in said denture and alginate on said base by inverting said denture onto said lower member of the articulator, to form a resilient cast;

holding the mandibular denture firmly to the articulator;

positioning the bite registration onto the mandibular denture;

placing the maxillary denture onto the bite registration;

pouring alginate through the opening in the upper member of the articulator onto the tissue bearing surface of the maxillary denture, thus forming a cast;

locking said denture to the articulator;

removing the bite registration from the dentures;

equilibrating the dentures.

7. A method of repairing a broken denture along adjacent surfaces thereof, said denture having a tissue bearing portion said method comprising the steps of:

pouring impression material over said tissue bearing portion to form therein a resilient cast of said tissue bearing portion;

removing said tissue bearing portion from said cast;

preparing said adjacent surfaces in the removed tissue bearing portion for repair;

reinserting said tissue bearing portion into said cast to hold the prepared surfaces in proper alignment with one another; and repairing the reinserted tissue bearing portion along the prepared surface portions thereof.

8. The method according to claim 7 further comprising the steps of:

placing a portion of impression material on a support platform; and joining said cast in an inverted position to said portion of impression material to form a firm base for repair of said denture.

9. The method according to claim 7 further comprising the steps of:

placing a portion of impression material on a support platform;

placing a cover having at least one aperture formed therein over said portion of impression material;

partially extruding said portion of material through said at least one aperture of said cover; and joining said cast in an inverted position to said portion of impression material extruded through said cover to form a firm base for repair of said denture.

10. The method according to claim 7 wherein:

said impression material is a non-reversible hydrocolloid compound.

11. A method of rapidly manufacturing a provisional denture for immediate placement after dental extractions in a dental patient's mouth, said method comprising the steps of:

utilizing an impression material to form an impression of the patient's oral cavity, said impression having tooth depressions therein;

placing a quick setting tooth-forming material in selected ones of said tooth depressions to form tooth portions of the provisional denture;

placing impression material into said impression and over said tooth portion to form a resilient cast;

removing said resilient cast from said impression;

temporarily securing said tooth portion to said resilient cast;

placing a base-forming quick setting acrylic material into the removed resilient cast to form a base portion of the provisional denture which is permanently secured to said artificial tooth portion thereof; and removing the base and artificial tooth portions from said cast to provide the provisional denture.

12. The method according to claim 11 further comprising the steps of:

placing a portion of impression material on a support platform; and joining said cast in an inverted position to said portion of resilient casting material on said support platform to hold the said cast firmly in place.

13. The method according to claim 11 wherein:

said artificial tooth forming material is acrylic.

14. The method according to claim 11 wherein:

said base forming material is acrylic.

15. The method according to claim 11 wherein:

said resilient casting material is a non-reversible hydrocolloid compound.

16. The method according to claim 15 wherein:

said non-reversible hydrocolloid compound is alginate.

17. A method of rapidly and accurately correcting occlusal discrepancies in a denture patient's bite by the mounting of dentures directly from the mouth to the support platform and pivot arm of an articulator for detection of prematurities and repair, said method comprising the steps of:

making an occlusal record of the patient's dentures within the mouth in centric relationship using a bite registration material;

removing the dentures from the mouth;

placing the lower denture into an impression material to form a resilient lower denture cast;

placing impression material on said support platform;

joining said lower denture cast to said impression material on said support platform for support thereof;

placing the upper denture into an impression material to form a resilient upper denture cast;

placing impression material on said pivot arm;

placing said occlusal record over said lower denture on said lower denture cast;

placing said upper denture over said occlusal record to properly align in centric relationship said upper denture and said lower denture;

joining said upper denture cast bearing said upper denture in proper alignment to the impression material on said pivot arm;

removing said occlusal record;

marking the prematurities on the dentures by opening and closing the pivot arm of the articulator; and, correcting the dentures by removal of the prematurities thereon.

18. The method according to claim 17 wherein:

said impression material is a non-reversible hydrocolloid compound.

19. The method according to claim 17 wherein:

said impression material is alginate.

20. A method of rapidly and accurately correcting occlusal discrepancies in a denture by mounting dentures directly from the mouth to the support platform and pivot arm of an articulator using a impression material, for detection of prematurities and repair thereof, said method comprising the steps of:

making an occlusal record of the patient's dentures within the mouth in centric relationship using a bite registration material;

pouring up the lower denture into a impression material to form a resilient lower denture cast;

joining said lower denture cast having said lower denture thereon to said support platform for support thereof;

pouring up the upper denture into a impression material to form a resilient upper denture cast;

placing said occlusal record in alignment over said lower denture cast;

placing said upper denture in alignment over said occlusal record to thereby orient said upper denture and lower denture in proper centric relationship;

joining said upper denture cast and upper denture attached thereto to said pivot arm;

removing said occlusal record;

marking the prematurities on the dentures by opening and closing said pivot arm on the articulator;

equilibrating the dentures by removal of the prematurities thereon.

21. The method according to claim 20 further comprising the steps of:
   placing impression material on said support platform;
   joining said lower denture cast to said impression material on said support platform;
   placing impression material on said pivot arm;
   joining said upper denture cast to said impression material on said pivot arm without disturbing the centric relationship between the upper and lower dentures.

22. The method according to claim 20 wherein:
   said impression material is a non-reversible hydrocolloid compound.

23. The method according to claim 20 wherein:
   said impression material is alginate.

24. A method for formation of a resilient cast of a denture for use in fabrication repair or modification procedures for dentures wherein alginate in a fluid state is poured into an impression of an oral cavity, and upon gelation becomes a semi-solid to form a resilient denture cast.

* * * * *